United States Patent
Burattin et al.

(10) Patent No.: US 6,469,194 B2
(45) Date of Patent: Oct. 22, 2002

(54) PRODUCTION OF NITRILES VIA HYDROCYANATION OF ETHYLENICALLY UNSATURATED ORGANIC COMPOUNDS

(75) Inventors: Paolo Burattin, Lyons; Pierre Coqueret, Francheville; Marc Huser, Villeurbanne, all of (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/886,288

(22) Filed: Jun. 22, 2001

(65) Prior Publication Data
US 2002/0022736 A1 Feb. 21, 2002

Related U.S. Application Data

(63) Continuation of application No. PCT/FR99/03231, filed on Dec. 21, 1999.

(51) Int. Cl.[7] ............................................. C07C 253/00
(52) U.S. Cl. ..................................................... 558/338
(58) Field of Search ........................................ 558/338

(56) References Cited

U.S. PATENT DOCUMENTS

| | | |
|---|---|---|
| 4,082,811 A | 4/1978 | Shook, Jr. |
| 4,539,302 A | 9/1985 | Leyendecker et al. |
| 4,990,645 A | 2/1991 | Back et al. |
| 5,488,129 A | 1/1996 | Huser et al. |
| 5,856,555 A | 1/1999 | Huser et al. |

FOREIGN PATENT DOCUMENTS

| | | |
|---|---|---|
| EP | 0 650 959 | 5/1995 |
| EP | 0 715 890 | 6/1996 |
| FR | 1599761 | 8/1970 |
| FR | 2338253 | 8/1977 |
| WO | 97/12857 | 4/1997 |
| WO | 97/24184 | 7/1997 |

OTHER PUBLICATIONS

Olah, G.A., et al., Friedel–Crafts and Related Reactions 188–199 (1963).

The Bibliographic material, including the Table of Contents, for vol. I and II, of Houben–Weyl, " *Methoden der organischen Chemie*, organische Phosphor Verbindungen," Methods of Organic Chemistry, "Organic Phosphorus Compounds," Part 1 (1963).

*Primary Examiner*—T. A. Solola
*Assistant Examiner*—Joseph Murray
(74) *Attorney, Agent, or Firm*—Burns, Doane, Swecker & Mathis, L.L.P.

(57) ABSTRACT

Ethylenically unsaturated organic compounds, for example diolefins, olefinic nitriles and monoolefins, are noncontaminatingly hydrocyanated into corresponding nitriles by (a) reacting such ethylenically unsaturated organic compounds with hydrogen cyanide in the presence of an aqueous solution containing a catalytically effective amount of a catalyst which comprises at least one nickel compound and at least one water-soluble phosphine, (b) thereafter separating the organic phase from the aqueous phase which result, the separated aqueous phase comprising a solid phase formed during hydrocyanation, and (c) thence treating the separated aqueous phase, or a solid phase removed therefrom, with hydrogen cyanide to thus at least partially dissolve said solid phase contained therein or removed therefrom.

14 Claims, No Drawings

PRODUCTION OF NITRILES VIA HYDROCYANATION OF ETHYLENICALLY UNSATURATED ORGANIC COMPOUNDS

CROSS-REFERENCE TO PRIORITY/PCT APPLICATIONS

This application claims priority under 35 U.S.C. § 119 of FR-98/16468, filed Dec. 22, 1998, and is a continuation of PCT/FR99/03231, filed Dec. 21, 1999 and designating the United States (published in the French language on Jun. 29, 2000 as WO 00/37431; the title and abstract were also published in English), both hereby expressly incorporated by reference.

CROSS-REFERENCE TO COMPANION APPLICATION

Our copending application Ser. No. 09/886,289, filed concurrently herewith, assigned to the assignee hereof and also expressly incorporated by reference.

BACKGROUND OF THE INVENTION

1. Technical Field of the Invention

The present invention relates to the hydrocyanation of ethylenically unsaturated organic compounds for the preparation of nitriles and, more particularly, to the hydrocyanation of diolefins or of substituted olefins for the production of dinitriles and/or to the isomerization of nitriles obtained via hydrocyanation.

The present invention relates more especially to hydrocyanation reactions catalyzed by nickel-based compounds.

2. Description of the Prior Art

French Patent No. 1,599,761 describes a process for the preparation of nitriles by addition of hydrocyanic acid to organic compounds containing at least one ethylenic double bond in the presence of a nickel catalyst and of a triaryl phosphite. This reaction can be carried out in the presence or in the absence of a solvent.

When a solvent is used in this process of the prior art, it is preferably a hydrocarbon, such as benzene or xylenes, or a nitrile, such as acetonitrile.

The catalyst employed is an organic nickel complex comprising ligands such as phosphines, arsines, stilbines, phosphites, arsenites or antimonites.

The presence of a promoter to activate the catalyst, such as a boron compound or a metal salt, generally a Lewis acid, is also recommended.

The hydrocyanation of compounds having at least one site of ethylenic unsaturation in the presence of an aqueous solution of a compound of a transition metal, in particular nickel, palladium or iron, and of a sulfonated phosphine, is described in FR-2,338,253.

The sulfonated phosphines described in this '253 patent are sulfonated triarylphosphines and more particularly sulfonated triphenylphosphines.

This process permits satisfactory hydrocyanation, in particular of butadiene and pentenenitriles, and an easy separation of the catalytic solution by a simple separation by settling and, consequently, avoids as far as possible the discharge of effluents or of waste comprising metals serving as catalysts.

However, in these processes, the overall lifetime of the catalyst is adversely affected by a loss of nickel during each sequence of the catalyst in the reactor. This loss is due, in particular, to a nickel hydroxide precipitate. This precipitate is also disadvantageous in the operation of the process as it contaminates the manufacturing plants, requiring either periodic cleaning of the latter or a stage of separation and removal of the precipitate. In the latter embodiment, an environmentally harmful effluent is produced.

SUMMARY OF THE INVENTION

Accordingly, a major object of the present invention is the provision of an improved hydrocyanation process which permits treating the precipitate indicated above, on the one hand to eliminate the risks of contamination of the production facility or of the environment and, on the other, to decrease the losses of catalyst.

Briefly, the present invention features a process for the hydrocyanation of ethylenically unsaturated organic compounds via reaction with hydrogen cyanide in the presence of an aqueous solution of a catalyst comprising at least one nickel compound and at least one water-soluble phosphine and, after reaction, separation of the organic and aqueous phases.

The process of the invention entails treating the recovered aqueous phase, which comprises a solid phase (colloids, gel or solid in suspension, or precipitated) formed during the hydrocyanation reaction, with hydrogen cyanide in order to dissolve said solid phase.

Thus, the aqueous phase can be recycled at least partially in the reactor without contaminating the production facility.

In another embodiment of the invention, the recovered aqueous phase A comprising the solid phase formed is subjected to a separation stage in order to extract the solid phase, the purified or clarified aqueous phase $A_1$ subsequently being at least partially recycled in the hydrocyanation reactor, the solid phase being dissolved by treatment with hydrogen cyanide.

DETAILED DESCRIPTION OF BEST MODE AND SPECIFIC/PREFERRED EMBODIMENTS OF THE INVENTION

More particularly according to the present invention, in a preferred embodiment thereof, the treatment of the separated solid phase with hydrogen cyanide is carried out in the presence of an aqueous solution comprising a water-soluble phosphine. The solution B thus recovered is, in another preferred embodiment, conveyed to a stage of regeneration of the catalyst which includes, in sum, a reduction of nickel in the (II) oxidation state to nickel in the (O) oxidation state. This reduction is carried out advantageously after addition of nickel in the (O) oxidation state to the solution obtained by dissolution of the solid phase.

In another preferred embodiment of the invention, the solution B is mixed with at least a portion of the clarified aqueous solution $A_1$ before the reduction regeneration treatment. Thus, as this solution $A_1$ comprises nickel in the (O) oxidation state, regeneration of all of the catalyst is possible.

According to another embodiment of the invention, the treatment with hydrogen cyanide of the solid phase formed, either after clarification of the recovered liquid phase A or directly in this liquid phase, is carried out by addition of hydrogen cyanide to the aqueous solution advantageously comprising a water-soluble phosphine or hydrocyanation catalyst and stirring the reaction mixture for the time necessary for the, preferably complete, dissolution of the precipitate.

The temperature of the reaction mixture is advantageously less than 100° C., and preferably ranges from 20° C. to 80°

C. The hydrogen cyanide is added in liquid form or in solution in water, or in a solution of water-soluble phosphine.

The amount of hydrogen cyanide added is at least equal to the stoichiometric amount required for converting the precipitated or insoluble nickel into soluble nickel cyanide. This minimum amount can be determined as a function of the weight of precipitate to be dissolved and by considering that this precipitated or insoluble Ni is nickel hydroxide.

The amount of hydrogen cyanide added will advantageously be from 30% to 400% greater than the stoichiometric amount.

The stage of regeneration of the catalyst, or, stated differently, the reduction of the nickel to the 0 oxidation state, can be carried out by several processes, such as a reduction by gaseous hydrogen, an electrochemical reduction, or addition of an organic or inorganic reducing agent. The reduction processes are known and are described, in particular, in WO 97/24184, EP 0,715,890 and FR 1,599,761.

Suitable water-soluble phosphine compounds include those compounds described in FR-2,338,253 or in WO 97/12857 and EP 0,650,959. These are exemplary only and not limiting.

Thus, suitable phosphines according to this invention have the following structural formula (I):

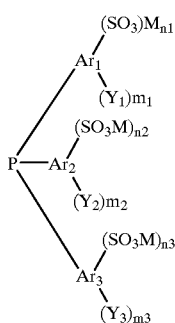

(I)

in which $Ar_1$, $Ar_2$ and $Ar_3$, which may be identical or different, are each an aryl radical; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN group, an $NO_2$ group, an OH group, an $NR_1R_2$ radical, wherein $R_1$ and $R_2$, which may be identical or different, are each an alkyl radical having from 1 to 4 carbon atoms; M is an inorganic or organic cationic residue selected, such that the compound of formula (I) is soluble in water, from the group consisting of $H^+$, cations derived from alkali metals or alkaline earth metals, $N(R_3R_4R_5R_6)^+$, wherein $R_3$, $R_4$, $R_5$ and $R_6$, which may be identical or different, are each an alkyl radical having from 1 to 4 carbon atoms or a hydrogen atom, and other metal cations, the benzenesulfonic acid salts of which are soluble in water; $m_1$, $m_2$ and $m_3$ which may be identical or different, are each an integer ranging from 0 to 5; and $n_1$, $n_2$ and $n_3$, which may be identical or different, are each an integer ranging from 0 to 3, at least one of these being equal to or greater than 1.

Exemplary metals, the benzenesulfonic acid salts of which are soluble in water, include lead, zinc and tin.

By the expression "soluble in water" is generally intended a compound soluble to at least 0.01 g per liter of water.

Preferred phosphines of formula (I) are those in which:
$Ar_1$, $Ar_2$ and $Ar_3$ are phenyl radicals;
$Y_1$, $Y_2$ and $Y_3$ are alkyl radicals having from 1 to 2 carbon atoms, or alkoxy radicals having from 1 to 2 carbon atoms;
M is a cation selected from the group consisting of $H^+$, cations derived from Na, K, Ca and Ba, $NH_4^+$, and tetramethylammonium, tetraethylammonium, tetrapropylammonium and tetrabutylammonium cations;
$m_1$, $m_2$ and $m_3$ are integers ranging from 0 to 3; and
$n_1$, $n_2$ and $n_3$ are integers ranging from 0 to 3, at least one also being greater than 1.

The more particularly preferred phosphines are the sodium, potassium, calcium, barium, ammonium, tetramethylammonium and tetraethylammonium salts of mono (sulfophenyl)diphenylphosphine, di(sulfophenyl)phenylphosphine and tri(sulfophenyl)phosphine, in which the $SO_3$ groups are preferably in the meta-position.

Exemplary phosphines of formula (I) according to the process of the invention are alkali metal or alkaline earth metal salts, ammonium salts, or quaternary ammonium salts of (3-sulfo-4-methylphenyl)di(4-methylphenyl)phosphine, (3-sulfo-4-methoxyphenyl)di(4-methoxyphenyl)phosphine, (3-sulfo-4-chlorophenyl)di(4-chlorophenyl)phosphine, di(3-sulfophenyl)phenylphosphine, di(4-sulfophenyl)phenylphosphine, di(3-sulfo-4-methylphenyl)(4-methylphenyl)phosphine, di(3-sulfo-4-methoxyphenyl)(4-methoxyphenyl)phosphine, di(3-sulfo-4-chlorophenyl)(4-chlorophenyl)phosphine, tri(3-sulfophenyl)phosphine, tri(4-sulfophenyl)phosphine, tri(3-sulfo-4-methylphenyl)phosphine, tri(3-sulfo-4-methoxyphenyl)phosphine, tri(3-sulfo-4-chlorophenyl)phosphine, (2-sulfo-4-methylphenyl)(3-sulfo-4-methylphenyl)(3,5-disulfo-4-methylphenyl)phosphine or (3-sulfophenyl)(3-sulfo-4-chlorophenyl)(3,5-disulfo-4-chlorophenyl)phosphine.

A mixture of these phosphines can of course be employed, in particular a mixture of mono-, di- and tri-meta-sulfonated phosphines.

Monodentate and bidentate phosphines having the following structural formulae (II) and (III) are also suitable according to the present invention:

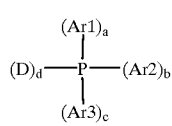

(II)

in which Ar1 and Ar2, which may be identical or different, are each aryl radicals or substituted such aryl radicals bearing one or more substituents, such as alkyl or alkoxy radicals having from 1 to 4 carbon atoms, halogen atoms, hydrophilic groups, such as —COOM, —$SO_3$M or —$PO_3$M, wherein M is an inorganic or organic cationic residue selected from among hydrogen, cations derived from alkali metals or alkaline earth metals, ammonium cations —$N(R)_4$, wherein the radicals R, which may be identical or different, are each a hydrogen atom or an alkyl radical having from 1 to 4 carbon atoms, and other cations derived from metals, the arylcarboxylic acid, arylsulfonic acid or arylphosphonic acid salts of which are soluble in water, —$N(R)_4$, wherein the radicals R, which may be identical or different, are each a hydrogen atom or an alkyl radical having from 1 to 4 carbon atoms, or —OH; $Ar_3$ is a substituted aryl radical bearing one or more substituents, such as alkyl or alkoxy radicals having from 1 to 4 carbon atoms, halogen atoms, hydrophilic groups, such as —COOM or —PO$_3$M, wherein M is an inorganic or organic cationic residue selected from among hydrogen, cations derived from alkali metals or alkaline earth metals, ammonium cations —N(R)$_4$, wherein the radicals R, which may be identical or different, are each a hydrogen atom or an alkyl radical having from 1 to 4 carbon atoms, and other metal cations, the arylcarboxylic acid or arylphosphonic acid salts of which are soluble in water, N(R)$_4$, wherein the radicals R, which may be identical or different, are each a hydrogen atom or an alkyl radical having from 1 to 4 carbon atoms, or —OH, with the proviso that at least one of the substituents of Ar$_3$ is a hydrophilic group as defined above; a is 0 or 1; b is 0 or 1; c is an integer ranging from 0 to 3; D is an alkyl radical, a cycloalkyl radical or an alkyl or cycloalkyl radical substituted by one or more substituents, such as an alkoxy radical having from 1 to 4 carbon atoms, a halogen atom, a hydrophilic group, such as —COOM, —SO$_3$M or —PO$_3$M, wherein M is an inorganic or organic cationic residue selected from among hydrogen, cations derived from alkali metals or alkaline earth metals, ammonium cations —N(R)$_4$, wherein the radicals R, which may be identical or different, are each a hydrogen atom or an alkyl radical having from 1 to 4 carbon atoms, and other metal cations, the arylcarboxylic acid, arylsulfonic acid or arylphosphonic acid salts of which are soluble in water, —N(R)$_4$, wherein the radicals R, which may be identical or different, are each a hydrogen atom or an alkyl radical having from 1 to 4 carbon atoms, or —OH; d is an integer ranging from 0 to 3; and the sum (a+b+c+d) is equal to 3; and

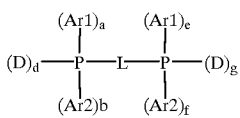

(III)

in which Ar1, Ar2 and D are as defined above for the formula (II); a, b, e, and f are each 0 or 1; d and g are each an integer ranging from 0 to 2; the sum (a+b+d) is equal to 2; the sum (e+f+g) is equal to 2; and L is a single valency bond or a divalent hydrocarbonaceous radical, such as an alkylene radical, a cycloalkylene radical, an arylene radical, or a radical deriving from a heterocycle comprising one or two oxygen, nitrogen or sulfur atoms in the ring, these various cyclic radicals being bonded directly to one of the phosphorus atoms or both phosphorus atoms or being bonded to one of the phosphorus atoms or to both via a linear or branched alkylene radical having from 1 to 4 carbon atoms, with the proviso that the ring or rings which are optionally moieties of the divalent radical L may comprise one or more substituents, such as an alkyl radical having from 1 to 4 carbon atoms.

Exemplary phosphines of structural formula (II) include tris(hydroxymethyl)phosphine, tris(2-hydroxyethyl)phosphine, tris(3-hydroxypropyl)phosphine, tris(2-carboxymethyl)phosphine, the sodium salt of tris(3-carboxyphenyl)phosphine, tris(3-carboxyethyl)phosphine, tris(4-trimethylammoniophenyl)phosphine iodide, the sodium salt of tris(2-phosphonoethyl)phosphine or bis(2-carboxyethyl)phenylphosphine.

And exemplary phosphines of structural formula (III) include the sodium salt of 2,2'-bis[di(sulfophenyl)phosphino]-1,1'-binaphthyl, the sodium salt of 1,2-bis[di(sulfophenyl)phosphinomethyl]cyclobutane (CBDTS), 1,2-bis(dihydroxymethylphosphino)ethane, 1,3-bis(dihydroxymethylphosphino)propane, or the sodium salt of 2,2'-bis [di(sulfophenyl)phosphinomethyl]-1,1'-binaphthyl.

Certain of the water-soluble phosphines of formulae (I) to (III) are commercially available.

For the preparation of the others, reference is made to the general or specific processes for the synthesis of phosphines described in the general literature, such as Houben-Weyl, *Methoden der organischen Chemie,* "organische Phosphor Verbindungen" [*Methods of Organic Chemistry,* "Organic Phosphorus Compounds"], Part 1 (1963).

Lastly, for the preparation of water-soluble derivatives which have not been described, starting from phosphines not comprising water-soluble substituents described above, one or more of these hydrophilic substituents are introduced. Thus, sulfonate groups, for example, may be introduced by the reaction of SO$_3$ in sulfuric acid. Carboxylate, phosphonate and quaternary ammonium groups can likewise be introduced via the usual chemical techniques for this type of synthesis.

The ethylenically unsaturated organic compounds which can be subjected to hydrocyanation in the presence of a catalyst according to the process of the invention are typically diolefins, such as butadiene, isoprene, 1,5-hexadiene or 1,5-cyclooctadiene; ethylenically unsaturated aliphatic nitriles, particularly linear pentenenitriles, such as 3-pentenenitrile or 4-pentenenitrile; monoolefins, such as styrene, methylstyrene, vinylnaphthalene, cyclohexene or methylcyclohexene; and mixtures of several of these compounds.

The pentenenitriles, in particular, can contain amounts, generally minor amounts, of other compounds, such as 2-methyl-2-butenenitrile, 2-methyl-2-butenenitrile, 2-pentenenitrile, valeronitrile, adiponitrile, 2-methylglutaronitrile, 2-ethylsuccinonitrile or butadiene, originating, for example, from the prior hydrocyanation reaction of butadiene.

Not insignificant amounts of 2-methyl-3-butenenitrile and 2-methyl-2-butenenitrile are formed, with the linear pentenenitriles, during the hydrocyanation of butadiene.

The catalytic solution employed in the hydrocyanation according to the process of the invention can be prepared before it is introduced into the reaction zone, for example by addition, to the aqueous solution of the water-soluble phosphine of formulae (I) to (III), of the appropriate amount of selected transition metal compound and, optionally, of the reducing agent. It is also possible to prepare the catalytic solution in situ by simple mixing of these various constituents.

The amount of nickel compound used is advantageously selected such that there is present, per liter of reaction solution, of from $10^{-4}$ to 1 and preferably from 0.005 to 0.5 mol of nickel.

The amount of water-soluble phosphine of formulae (I) to (III) used to prepare the reaction solution is advantageously selected such that the number of moles of this compound with respect to 1 mol of nickel ranges from 0.5 to 2,000 and preferably from 2 to 300.

Exemplary nickel compounds include:
(i) compounds in which the nickel is in the zero oxidation state, such as potassium tetracyanonickelate K$_4$[Ni(CN)$_4$], bis(acrylonitrile)nickel(O), bis(1,5-cyclooctadiene)$_2$nickel and derivatives comprising ligands from Group Va of the Periodic Table, such as tetrakis(triphenylphosphine)nickel(O) (in the latter case, the compound can be dissolved in a water-immiscible solvent, such as toluene, and then an aqueous solution of sulfonated phosphine extracts part of the nickel, a red coloration developing in the aqueous solution which separates by settling);

(ii) nickel compounds, such as carboxylates (in particular the acetate), carbonate, bicarbonate, borate, bromide, chloride, citrate, thiocyanate, cyanide, formate, hydroxide, hydrophosphite, phosphate, phosphate and derivatives, iodide, nitrate, sulfate, sulfite, arylsulfonates and alkylsulfonates.

It is not necessary for the nickel compound itself to be soluble in water. For example, nickel cyanide, one of the preferred compounds, which is sparingly soluble in water, can be dissolved in an aqueous solution of phosphine.

When the nickel compound used corresponds to a nickel oxidation state of greater than 0, the catalyst is subjected to a chemical or electrochemical reduction stage, as indicated above.

Although the reaction is generally carried out without a third solvent, it can be advantageous to add an inert water-immiscible organic solvent which can be that of the subsequent extraction.

Exemplary such solvents are aromatic, aliphatic or cycloaliphatic hydrocarbons which maintain the reaction mixture in the two-phase state.

Thus, once the reaction is complete, it is very easy to separate, on the one hand, an aqueous phase comprising water-soluble phosphines and the nickel compound and, on the other, an organic phase comprising the reactants involved in the reaction, the reaction products and, if appropriate, the water-immiscible organic solvent.

The hydrocyanation reaction is advantageously carried out at a temperature of 10° C. to 200° C. and preferably of 30° C. to 120° C.

The process of the invention can be carried out continuously or batchwise.

The hydrogen cyanide employed can be prepared from metal cyanides, in particular sodium cyanide, or cyanohydrins.

The hydrogen cyanide is introduced into the reactor in the gaseous form or in the liquid form. It can also be dissolved beforehand in an organic solvent.

In the batchwise embodiment, it is possible in practice, to charge into a reactor which has been purged beforehand using an inert gas (such as nitrogen or argon) either an aqueous solution comprising all or part of the various constituents, such as the water-soluble phosphine, the transition metal compound, the optional reducing agent and the optional solvent, or the said constituents separately. Generally, the reactor is then heated to the desired temperature and then the compound to be hydrocyanated is introduced. The hydrogen cyanide is then itself introduced, preferably continuously and uniformly.

When the reaction (the progress of which can be monitored by quantitative determination of samples withdrawn) is complete, the reaction mixture is drawn off after cooling and the reaction products are isolated by separation by settling, optionally followed by extraction of the aqueous layer using an appropriate solvent, such as, for example, the abovementioned water-immiscible solvents.

The aqueous catalytic solution can then be recycled to a fresh reaction for the hydrocyanation of organic compounds comprising at least one ethylenic double bond, after having been treated in accordance with the process of the invention.

It is also possible to use the catalyst in combination with a Lewis acid.

The Lewis acid comprising the cocatalyst makes it possible in particular, in the case of the hydrocyanation of ethylenically unsaturated aliphatic nitriles, to improve the linearity of the dinitriles obtained, namely, the percentage of linear dinitrile with respect to all of the dinitriles formed, and/or to increase the lifetime of the catalyst.

By the term "Lewis acid" is intended the usual definition, namely, compounds which are electron-pair acceptors.

The Lewis acids noted in the work edited by G. A. Olah, "Friedel-Crafts and Related Reactions", Volume I, pages 191 to 197 (1963), are particularly representative.

The Lewis acids which can be employed as cocatalysts in the subject process are advantageously selected from among compounds of the elements from Groups Ib, IIb, IIIa, IIIb, IVa, IVb, Va, Vb, VIb, VIIb and VIII of the Periodic Classification of the Elements, insofar as said compounds are at least partially soluble in water. These compounds are generally salts, in particular halides, preferably chlorides and bromides, sulfates, carboxylates and phosphates.

Exemplary such Lewis acids include zinc chloride, zinc bromide, zinc iodide, manganese chloride, manganese bromide, cadmium chloride, cadmium bromide, stannous chloride, stannous bromide, stannous sulfate, stannous tartrate, chlorides or bromides of rare earth metal elements, such as lanthanum, cerium, praseodymium, neodymium, samarium, europium, gadolinium, terbium, dysprosium, holmium, erbium, thulium, ytterbium and lutetium, cobalt chloride, ferrous chloride or yttrium chloride.

It is, of course, possible to employ mixtures of several Lewis acids.

It is also advantageous, if appropriate, to stabilize the Lewis acid in aqueous solution by the addition of an alkali metal or alkaline earth metal halide, such as lithium chloride, sodium chloride, calcium chloride or magnesium chloride, in particular. The alkali metal or alkaline earth metal halide/Lewis acid molar ratio varies very widely, for example from 0 to 100, it being possible for the specific ratio to be adjusted depending on the stability of the Lewis acid in water.

Very particularly preferred Lewis acids include zinc chloride, zinc bromide, stannous chloride, stannous bromide, stannous chloride stabilized with lithium chloride, stannous chloride stabilized with sodium chloride and zinc chloride/stannous chloride mixtures.

The Lewis acid cocatalyst employed generally constitutes from 0.01 to 50 mol per mole of nickel compound and preferably from 1 to 10 mol per mole.

As regards the implementation of the process of the invention, the catalytic solution employed for the hydrocyanation in the presence of Lewis acid can be prepared before it is introduced into the reaction region, for example by addition, to the aqueous solution of the water-soluble phosphine, of the appropriate amount of nickel hydroxide, of the Lewis acid and optionally of the reducing agent.

It is also possible, under the conditions of the hydrocyanation process of the present invention, and in particular by carrying out the reaction in the presence of the catalyst described above comprising at least one water-soluble phosphine and at least one nickel compound, to isomerize 2-methyl-3-butenenitrile to pentenenitriles in the absence of hydrogen cyanide.

The 2-methyl-3-butenenitrile subjected to the isomerization according to the invention can be employed alone or as a mixture with other compounds.

Thus, it is possible to employ 2-methyl-3-butenenitrile as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

Thus, it is particularly advantageous to treat the reaction mixture originating from the hydrocyanation of butadiene with HCN in the presence of an aqueous solution of at least one water-soluble phosphine and of at least one nickel compound, more preferably of a nickel compound in the 0 oxidation state, as described above.

In this preferred embodiment, as the catalytic system is already present for the hydrocyanation reaction of butadiene, it is sufficient to terminate any introduction of hydrogen cyanide in order to allow the isomerization reaction to take place.

It is possible, if appropriate in this embodiment, to gently flush the reactor using an inert gas, such as nitrogen or argon, for example, in order to drive off the hydrocyanic acid which might still be present.

The isomerization reaction is generally carried out at a temperature of from 10° C. to 200° C. and preferably from 60° C. to 120° C.

In the preferred embodiment of an isomerization immediately following the hydrocyanation reaction of butadiene, it will be advantageous to carry out the isomerization at the temperature at which the hydrocyanation has been carried out.

As regards the process for the hydrocyanation of ethylenically unsaturated compounds, the catalytic solution used for the isomerization can be prepared before it is introduced into the reaction zone, for example by addition, to the aqueous solution of a water-soluble phosphine, of the appropriate amount of nickel compound and optionally of the reducing agent. It is also possible to prepare the catalytic solution in situ by simple mixing of these various constituents. The amount of nickel compound and the amount of water-soluble phosphine are the same as for the hydrocyanation reaction.

Although the isomerization reaction is generally carried out without a third solvent, it can be advantageous to add an inert water-immiscible organic solvent which can be that of the subsequent extraction. This is, in particular, the case when such a solvent has been employed in the hydrocyanation reaction of butadiene which has been used to prepare the mixture subjected to the isomerization reaction. Such solvents are advantageously selected from among those which have been indicated above for the hydrocyanation.

At the end of the reaction, it is very easy to separate the catalyst from the isomerization reaction products, as has been indicated for the hydrocyanation, and to recycle it, if appropriate, in one of the hydrocyanation reactions described above or in a fresh isomerization reaction, after treatment of the aqueous phase and/or of the solid phase according to the process of the invention with hydrogen cyanide in order to dissolve said solid phase.

In order to further illustrate the present invention and the advantages thereof, the following specific examples are given, it being understood that same are intended only as illustrative and in nowise limitative.

EXAMPLE 1

(1) Preparation of the Ni/TSTPP Catalytic Solution:

500 cm$^3$ of a solution of 350 mmol of sodium salt of trisulfonated triphenylphosphine (TSTPP) in water were charged into a 1 liter round-bottomed glass flask equipped with a magnetic bar and an ascending reflux condenser; this solution was degassed. 21.40 g (78 mmol) of Ni (cyclooctadiene)$_2$ and then 350 cm$^3$ of ortho-xylene, degassed beforehand, were subsequently introduced with stirring and under a stream of argon.

The mixture was heated at 45° C. for 15 hours (h). After cooling, the two-phase system was separated by settling and the aqueous phase, which was deeply colored red, was withdrawn. Its Ni concentration, determined by analysis, was 134 mmol/kg.

(2) Isomerizaton of 2-methyl-3-butenenitrile:

The following materials were charged into a 2 liter glass reactor purged under argon and stirred using a turbine:

2-methyl-3-butenenitrile (2M3BN): 770 g (9.50 mol), the catalytic solution: 250 cm$^3$ (39.5 mmol of Ni and 175.5 mmol of TSTPP).

The reaction mixture was stirred for 1.5 h at 90° C. After cooling and separation by settling, the final organic phase was quantitatively determined by gas chromatography (GC).

The following results were obtained:

Degree of conversion (DC) of the 2M3BN: 95%

Yield (Yd) of 3-pentenenitrile (3PN) with respect to the 2M3BN converted: 91.5%

Yield (Yd) of 2-methyl-2-butenenitrile (2M2BN) with respect to the 2M33N converted: 8%

The aqueous phase recovered after separation by settling exhibited a slight precipitate (finely divided solid phase in suspension). On standing, the latter slowly settled out in the form of a brown-colored film which readily redispersed with stirring. Quantitative determination of the Ni on a withdrawn aqueous sample filtered by means of a Millipore Millex-HV® filter (Hydrophilic PVDF, 0.45 μm) provided the following Ni concentration: 110 mmol/kg.

(3) Treatment of the Aqueous Suspension:

35 cm$^3$ of the aqueous suspension indicated above (§ 2) were charged into a 150 cm$^3$ glass reactor purged with argon and equipped with an auto-suction turbine. With stirring (1200 revolutions/minute) at room temperature, 0.265 ml of hydrocyanic acid was injected into the reactor head space, with a constant flow rate and over a duration of one hour, via a syringe thermostatically controlled at −10° C. After injection of the HCN, the mixture was maintained stirred for 1 hour at room temperature in a closed system and then the head space of the reactor was flushed with a flow of argon for an additional 1 hour, approximately. By this treatment, a homogeneous aqueous solution was obtained: no noticeable precipitate in the solution on standing. Quantitative determination of the total Ni and of the Ni(II), respectively, by elemental analysis and polarographic analysis, on a withdrawn sample filtered by means of a Millipore Millex-HV® filter (Hydrophilic PVDF, 0.45 μm) provided the following results: [Ni]=122 mmol/kg and [Ni (II)]=23 mmol/kg ([Ni$^0$]=99 mmol/kg).

EXAMPLE 2

35 cm$^3$ of the aqueous suspension indicated in Example 1, § 2, were charged into a 150 cm$^3$ glass reactor purged with argon and equipped with an auto-suction turbine. With stirring (1200 revolutions/minute) and at a temperature of 50° C., 0.265 ml of hydrocyanic acid was injected into the reactor head space, with a constant flow rate and over a duration of 1 hour, via a syringe thermostatically controlled at −10° C. After injection of the HCN and cooling to room temperature, the mixture was maintained stirred for 1 hour in a closed system and then the head space of the reactor was flushed with a flow of argon for an additional 1 hour, approximately. By this treatment, a homogeneous aqueous solution was obtained: no noticeable precipitate in the solution on standing. Quantitative determination of the total Ni and of the Ni(II), respectively, by elemental analysis and polarographic analysis, on a withdrawn sample filtered by means of a Millipore Millex-HV® filter (Hydrophilic PVDF, 0.45 μm) provided the following results:

[Ni]=129 mmol/kg and (Ni(II)]=38 mmol/kg ([NI$^0$]=91 mmol/kg).

EXAMPLE 3

35 cm$^3$ of the aqueous solution indicated in Example 1, § 2, were charged into a 150 cm$^3$ glass reactor purged with argon and equipped with an auto-suction turbine. With stirring (1200 revolutions/minute) and at a temperature of 70° C., 0.265 ml of hydrocyanic acid was injected into the reactor head space, with a constant flow rate and over a duration of 1 hour, via a syringe thermostatically controlled at −10° C. After injection of the HCN and cooling to room temperature, the mixture was maintained stirred for 1 hour in a closed system and then the head space of the reactor was flushed with a flow of argon for an additional 1 hour, approximately. By this treatment, a homogeneous aqueous solution was obtained: no noticeable precipitate in the solution on standing. Quantitative determination of the total Ni and of the Ni(II), respectively, by elemental analysis and polarographic analysis, on a withdrawn sample filtered by means of a Millipore Millex-HV® filter (Hydrophilic PVDF, 0.45 μm) provided the following results:

[Ni]=122 mmol/kg and [Ni(II)]=30 mmol/kg ([Ni$^0$]=92 mmol/kg).

EXAMPLE 4

35 cm$^3$ of the aqueous suspension indicated in Example 1, § 2, were charged into a 150 cm$^3$ glass reactor purged with argon and equipped with an auto-suction turbine. With stirring (1200 revolutions/minute) and at a temperature of 50° C., 0.295 ml of hydrocyanic acid was injected into the reactor head space, with a constant flow rate and over a duration of 1 hour, via a syringe thermostatically controlled at −10° C. After injection of the HCN and cooling to room temperature, the mixture was maintained for 1 hour in a closed system and then the head space of the reactor was flushed with a flow of argon for an additional 1 hour, approximately. By this treatment, a homogeneous aqueous solution was obtained: no noticeable precipitate in the solution on standing. Quantitative determination of the total Ni and of the Ni(II), respectively, by elemental analysis and polarographic analysis, on a withdrawn sample filtered by means of a Millipore Millex-HV® filter (Hydrophilic PVDF, 0.45 μm) provided the following results:

[Ni]=132 mmol/kg and [Ni (II)=40 mmol/kg [NI$^0$]=92 mmol/kg).

EXAMPLE 5

(1) Separation of the solid phase:

The aqueous phase recovered after separation by settling was filtered under an argon atmosphere through a sintered glass of porosity 4. The filtrate, stored under argon, had the form of a dark red homogeneous solution. A green paste was recovered on the sintered glass, which paste, dried under vacuum at room temperature for 12 h, resulted in a powder having a light green coloration. The X-ray diffraction diagram of the latter exhibited diffraction lines characteristic of crystalline Ni(OH)$_2$ and of the crystalline sodium salt of TSTPP. Elemental analysis of the powder in question indicated the following composition:

Ni: 11.7 wgt %; P: 3.7 wgt %; C: 27.6 wgt %; Na: 6.0 wgt %; N: <1 wgt %.

(2) Treatment of the solid phase:

35 cm$^3$ of a solution of 24.6 mmol of sodium salt of trisulfonated triphenylphosphine (TSTPP) in water were charged into a 150 cm$^3$ glass reactor purged with argon and equipped with an auto-suction turbine. This solution was degassed. 2.75 g of the light-green powder obtained above were subsequently introduced. With stirring (1200 revolutions/minute) and at room temperature, 0.540 ml of hydrocyanic acid was injected into the reactor head space, with a constant flow rate and over a duration of 1 hour, via a syringe thermostatically controlled at −10° C. During the injection of the HCN, the solution rapidly became orangey and then bright red. After injection, the mixture was maintained stirred for 3 hours at 80° C. and then cooled to room temperature, where it was maintained stirred for an additional 12 hours. After flushing the head space of the reactor with argon for approximately 1 hour, a clear and homogeneous solution having a dark red coloration was recovered. Quantitative determination of the Ni on a withdrawn sample filtered by means of a Millipore Millex-HV® filter (Hydrophilic PVDF, 0.45 μm) provided the following result: [Ni]=123 mmol/kg.

The solution thus recovered could be used as catalytic solution after having been subjected to a reduction regeneration stage after addition of nickel in the (O) oxidation state.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydrocyanation of an ethylenically unsaturated organic compound into a corresponding nitrile, said ethylenically unsaturated organic compound comprising a diolefin, an ethylenically unsaturated aliphatic nitrile, a monoolefin, or a mixture thereof, comprising (a) reacting said ethylenically unsaturated organic compound with hydrogen cyanide in the presence of an aqueous solution containing a catalytically effective amount of a catalyst which comprises at least one nickel compound and at least one water-soluble phosphine, (b) thereafter separating the resulting organic phase from the aqueous phase, said separated aqueous phase comprising a solid phase formed during the hydrocyanation, and (c) thence treating said separated aqueous phase, or a solid phase removed therefrom, with hydrogen cyanide to partially dissolve said solid phase contained therein or removed therefrom.

2. The process as defined by claim 1, which comprises (c) treating said separated aqueous phase with hydrogen cyanide to partially dissolve said solid phase contained therein, and (d) at least partially recycle said aqueous phase thus treated to the zone of hydrocyanation (a).

3. The process as defined by claim 2, which comprises (d) partially recycling said aqueous phase thus treated to the zone of hydrocyanation (a), and (e) regenerating the catalyst comprising that fraction of said aqueous phase not recycled.

4. The process as defined by claim 1, which comprises (c) treating with HCN a solid phase removed from said separated aqueous phase.

5. The process as defined by claim 1, which comprises reducing some of the nickel in the said solid phase that are in the (II) oxidation state, to nickel in the (O) oxidation state.

6. The process as defined by claim 5, which comprises admixing an aqueous solution obtained by treating said solid phase with HCN, prior to said stage of reduction, with at least a fraction of separated aqueous phase.

7. The process as defined by claim 5, comprising at least partially reducing said nickel (II) values with gaseous hydrogen.

8. The process as defined by claim 5, comprising at least partially reducing said nickel (II) values electrochemically.

9. The process as defined by claim 5, comprising at least partially reducing said nickel (II) values with a borohydride, magnesium or zinc reducing agent.

10. The process as defined by claim 1, comprising isomerizing the nitrile compound thus formed.

11. The process as defined by claim 1, said solid phase contained in said separated aqueous phase, or removed therefrom, comprises colloids, gel, solids in suspension, and/or a precipitate.

12. The process as defined by claim 1, which comprises (c) treating said separated aqueous phase, or solid phase removed therefrom, with HCN, to convert a portion of the nickel hydroxide into nickel cyanide.

13. The process as defined by claim 1, said ethylenically unsaturated organic compound comprising butadiene, isoprene, a hexadiene, a cyclooctadiene, a pentenenitrile, styrene, methylstyrene, vinylnaphthalene, cyclohexene, methcyclohexene, or mixture thereof.

14. The process as defined by claim 1, said aqueous solution containing a cocatalytically effective amount of a Lewis acid.

* * * * *